(12) United States Patent
McBride, Jr. et al.

(10) Patent No.: US 11,969,192 B2
(45) Date of Patent: Apr. 30, 2024

(54) SPINAL IMPLANT SYSTEM AND METHOD

(71) Applicant: WARSAW ORTHOPEDIC INC., Warsaw, IN (US)

(72) Inventors: Larry T. McBride, Jr., Memphis, TN (US); Bret M. Wilfong, Hernando, TN (US); Christel Italiaie, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 194 days.

(21) Appl. No.: 17/470,020

(22) Filed: Sep. 9, 2021

(65) Prior Publication Data

US 2021/0401471 A1 Dec. 30, 2021

Related U.S. Application Data

(63) Continuation of application No. 16/395,498, filed on Apr. 26, 2019, now Pat. No. 11,116,550.

(51) Int. Cl.
*A61B 17/70* (2006.01)
*A61B 17/00* (2006.01)

(52) U.S. Cl.
CPC ...... *A61B 17/7049* (2013.01); *A61B 17/7034* (2013.01); *A61B 17/7056* (2013.01); *A61B 2017/00477* (2013.01)

(58) Field of Classification Search
CPC ............ A61B 17/7001; A61B 17/7032; A61B 17/7034; A61B 17/7049; A61B 17/705; A61B 17/7052
USPC .................................................. 606/250–253
See application file for complete search history.

(56) References Cited

U.S. PATENT DOCUMENTS

| | | | |
|---|---|---|---|
| 5,403,314 A * | 4/1995 | Currier ............. | A61B 17/7004 403/396 |
| 6,050,997 A * | 4/2000 | Mullane ............ | A61B 17/7049 606/264 |
| 6,277,120 B1 | 8/2001 | Lawson | |
| 6,872,208 B1 | 3/2005 | McBride et al. | |
| 7,166,108 B2 | 1/2007 | Mazda et al. | |
| 7,481,828 B2 | 1/2009 | Mazda et al. | |

(Continued)

FOREIGN PATENT DOCUMENTS

| | | |
|---|---|---|
| EP | 2018827 A1 | 1/2009 |
| EP | 3295880 A1 | 3/2018 |
| WO | 1996039090 A1 | 12/1996 |

OTHER PUBLICATIONS

European Patent Office, 80298 Munich, Germany, Extended European Search Report, Application No. 20794503.1, dated Dec. 20, 2022.

*Primary Examiner* — Nicholas J Plionis
*Assistant Examiner* — Christina Negrellirodriguez
(74) *Attorney, Agent, or Firm* — Sorell, Lenna & Schmidt, LLP

(57) ABSTRACT

A spinal construct includes a body defining a transverse axis. The body includes a wall disposed between a first implant cavity and a second implant cavity. The body further defines a first opening communicating with the first implant cavity and a second opening communicating with the second implant cavity. The first opening defines a first axis and the second opening defines a second axis. At least one of the first axis and the second axis are disposed in a substantially non-perpendicular orientation relative to the transverse axis. Systems, surgical instruments, implants and methods are disclosed.

20 Claims, 9 Drawing Sheets

(56) References Cited

U.S. PATENT DOCUMENTS

| | | |
|---|---|---|
| 7,655,025 B2 | 2/2010 | Ritland |
| 7,959,654 B2 | 6/2011 | Mazda et al. |
| 8,021,399 B2 | 9/2011 | Ritland |
| 8,162,946 B2 | 4/2012 | Baccelli et al. |
| 8,172,843 B2 | 5/2012 | Baccelli et al. |
| 8,323,319 B2 | 12/2012 | Mazda et al. |
| 8,337,532 B1 | 12/2012 | McLean et al. |
| 8,430,918 B2 | 4/2013 | Baccelli et al. |
| 8,870,870 B2 | 10/2014 | Baccelli et al. |
| 8,926,668 B2 | 1/2015 | Douget |
| 8,936,625 B2 | 1/2015 | Larroque-Lahitette et al. |
| 10,383,663 B2 * | 8/2019 | Murray .............. A61B 17/7043 |
| 2002/0111625 A1 | 8/2002 | Richelsoph et al. |
| 2005/0131404 A1 | 6/2005 | Mazda et al. |
| 2007/0270817 A1 * | 11/2007 | Rezach .............. A61B 17/7049 606/252 |
| 2010/0249845 A1 | 9/2010 | Meunier et al. |
| 2011/0301644 A1 | 12/2011 | Belliard |
| 2012/0029571 A1 | 2/2012 | Schwab et al. |
| 2012/0271354 A1 | 10/2012 | Baccelli et al. |
| 2012/0303121 A1 | 11/2012 | Douget et al. |
| 2014/0094850 A1 | 4/2014 | Clement et al. |
| 2016/0166289 A1 * | 6/2016 | Alsup .................... A61B 17/70 606/253 |
| 2017/0086895 A1 * | 3/2017 | Barra ................ A61B 17/8605 |
| 2017/0280063 A1 * | 9/2017 | Jeon ....................... G06V 20/56 |
| 2017/0281247 A1 | 10/2017 | Murray et al. |
| 2018/0243009 A1 * | 8/2018 | Bobbitt .............. A61B 17/7049 |

* cited by examiner

SPINAL IMPLANT SYSTEM AND METHOD

CROSS REFERENCE TO RELATED APPLICATIONS

This application is a continuation of U.S. patent application Ser. No. 16/395,498, filed Apr. 26, 2019, which is expressly incorporated by reference herein, in its entirety.

TECHNICAL FIELD

The present disclosure generally relates to medical devices for the treatment of musculoskeletal disorders, and more particularly to a spinal implant system and a method for treating a spine.

BACKGROUND

Spinal pathologies and disorders such as scoliosis, kyphosis, and other curvature abnormalities, degenerative disc disease, disc herniation, osteoporosis, spondylolisthesis, stenosis, tumor and fracture may result from factors including trauma, disease and degenerative conditions caused by injury and aging. Spinal disorders typically result in symptoms including deformity, pain, nerve damage, and partial or complete loss of mobility.

Non-surgical treatments, such as medication, rehabilitation and exercise can be effective, however, may fail to relieve the symptoms associated with these disorders. Surgical treatment of these spinal disorders includes correction, fusion, fixation, discectomy, laminectomy and implantable prosthetics. As part of these surgical treatments, spinal constructs including vertebral rods are often used to provide stability to a treated region. Rods redirect stresses away from a damaged or defective region while healing takes place to restore proper alignment and generally support vertebral members. During surgical treatment, one or more rods and bone fasteners can be delivered to a surgical site. The rods may be attached via the fasteners to the exterior of two or more vertebral members. This disclosure describes an improvement over these prior technologies.

SUMMARY

In one embodiment, a spinal construct is provided. The spinal construct comprises a body defining a transverse axis. The body includes a wall disposed between a first implant cavity and a second implant cavity. The body further defines a first opening communicating with the first implant cavity and a second opening communicating with the second first implant cavity. The first opening defines a first axis and the second opening defines a second axis. At least one of the first axis and the second axis are disposed in a substantially non-perpendicular orientation relative to the transverse axis. In some embodiments, systems, surgical instruments, implants and methods are disclosed.

In one embodiment, the spinal construct comprises a connector including a body connectable with tissue and defining a transverse axis. The body includes a wall disposed between a first implant cavity and a second implant cavity. The body further defines a first opening communicating with the first implant cavity and a second opening communicating with the second implant cavity. The first opening defines a first axis and the second opening defines a second axis. At least one of the first axis and the second axis are disposed in a substantially non-perpendicular orientation relative to the transverse axis. A first spinal rod is disposable with the first implant cavity. A first coupling member is disposable with the first opening and engageable with the first spinal rod. A second spinal rod is disposable with the second implant cavity. A second coupling member is disposable with the second opening and engageable with the second spinal rod.

In one embodiment, the spinal construct comprises a body connectable with tissue and defining a transverse axis. The body includes a wall disposed between a first closed implant cavity and a second implant cavity. An end of a spinal rod is disposed in the closed implant cavity. The body further defines an opening communicating with the second implant cavity. The opening defines a first axis that is disposed in a substantially non-perpendicular orientation relative to the transverse axis.

BRIEF DESCRIPTION OF THE DRAWINGS

The present disclosure will become more readily apparent from the specific description accompanied by the following drawings, in which.

DETAILED DESCRIPTION

Figure 1:
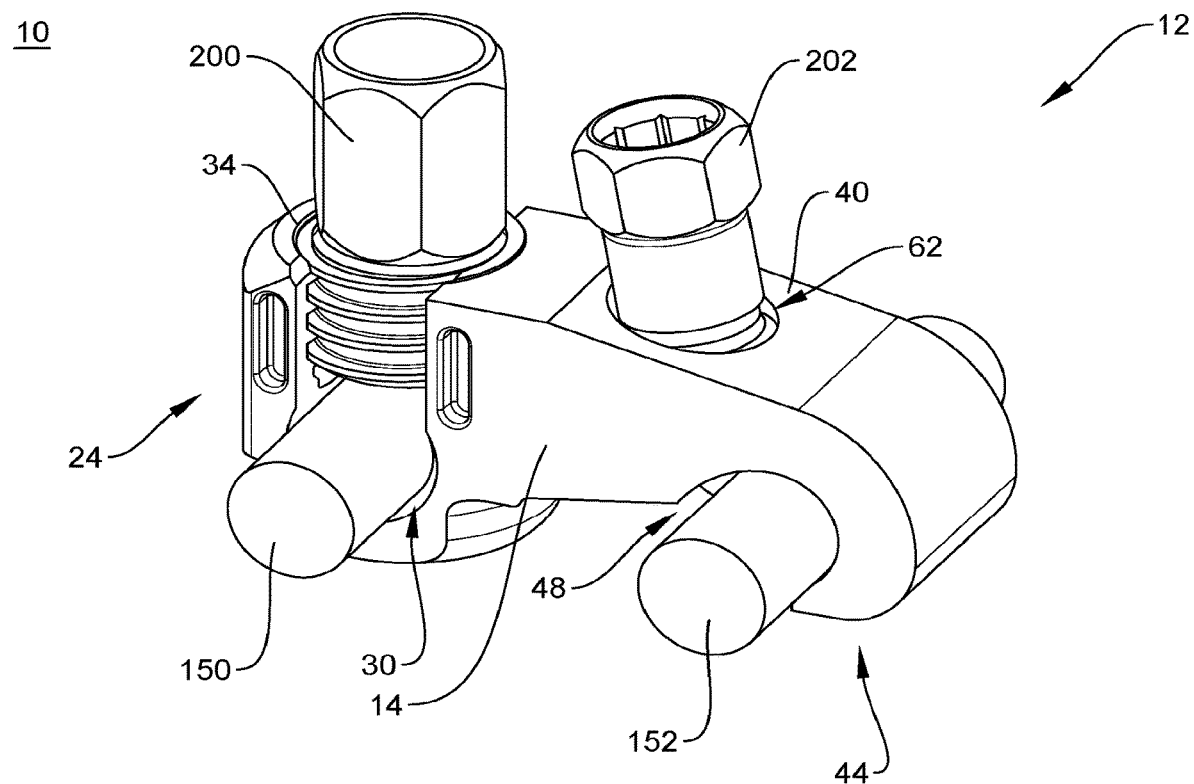
FIG. 1 is a perspective view of components of one embodiment of a spinal implant system in accordance with the principles of the present disclosure.

The exemplary embodiments of the surgical system and related methods of use disclosed are discussed in terms of medical devices for the treatment of musculoskeletal disorders and more particularly, in terms of a surgical system and method for treatment of a spine disorder. In some embodiments, the systems and methods of the present disclosure are employed with a spinal joint fusion, for example, with a cervical, thoracic, lumbar and/or sacral region of a spine.

In some embodiments, the present surgical system includes a spinal construct having a connector. In some embodiments, the connector includes a tulip hybrid cross-link connector. In some embodiments, the connector includes a top loading spinal rod passageway and a side loading spinal rod passageway. The connector is configured to connect a spinal rod with a spinal construct including, such as, for example, bone screws and a spinal rod. In some embodiments, the connector defines a transverse axis and includes a first implant cavity and a second implant cavity. In some embodiments, at least one of the implant cavities is configured for side loading a spinal rod. In some embodiments, the connector includes an opening communicating with the first implant cavity and an opening communicating with the second implant cavity.

In some embodiments, the connector includes a second opening angled towards the first opening to facilitate insertion of the connector through a small incision in a patient. In some embodiments, the connector is utilized with a cortical screw trajectory procedure. In some embodiments, the connector facilitates connecting spinal rods having a diameter of 4.75 mm by utilizing an angled second opening for connection of a set screw at the side loaded spinal rod. In some embodiments, the openings for the set screws are angled and not oriented perpendicular to a transverse axis of the connector, for example, disposed directly into the connector. In some embodiments, the openings for the set screws are disposed in substantially parallel relation. In some embodiments, the openings for the set screws are angled and not parallel. In some embodiments, a first set screw opening axis is disposed at an angle relative to the transverse axis of the connector and a second set screw opening axis oriented perpendicular to the transverse axis of the connector, for example, disposed directly into the connector. In some embodiments, the connector includes only one set screw opening, which is angled relative to the transverse axis of the connector. In some embodiments, the present surgical system includes a spinal construct having a connector with convergent angled set screw openings to facilitate a midline type cortical bone screw trajectory. In some embodiments, this configuration maintains surgical instruments in the same orientation throughout a surgical procedure while minimizing tissue exposure.

In some embodiments, one or all of the components of the surgical system may be disposable, peel-pack, pre-packed sterile devices. One or all of the components of the system may be reusable. The system may be configured as a kit with multiple sized and configured components.

In some embodiments, the surgical system of the present disclosure may be employed to treat spinal disorders such as, for example, degenerative disc disease, disc herniation, osteoporosis, spondylolisthesis, stenosis, scoliosis and other curvature abnormalities, kyphosis, tumor and fractures. In some embodiments, the surgical system of the present disclosure may be employed with other osteal and bone related applications, including those associated with diagnostics and therapeutics. In some embodiments, the disclosed surgical system may be alternatively employed in a surgical treatment with a patient in a prone or supine position, and/or employ various surgical approaches to the spine, including anterior, posterior, posterior mid-line, direct lateral, postero-lateral, and/or antero-lateral approaches, and in other body regions. The surgical system of the present disclosure may also be alternatively employed with procedures for treating the lumbar, cervical, thoracic, sacral and pelvic regions of a spinal column. The surgical system of the present disclosure may also be used on animals, bone models and other non-living substrates, such as, for example, in training, testing and demonstration.

The surgical system of the present disclosure may be understood more readily by reference to the following detailed description of the embodiments taken in connection with the accompanying drawing figures, which form a part of this disclosure. It is to be understood that this application is not limited to the specific devices, methods, conditions or parameters described and/or shown herein, and that the terminology used herein is for the purpose of describing particular embodiments by way of example only and is not intended to be limiting. In some embodiments, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

As used in the specification and including the appended claims, "treating" or "treatment" of a disease or condition refers to performing a procedure that may include administering one or more drugs to a patient (human, normal or otherwise or other mammal), employing implantable devices, and/or employing instruments that treat the disease, such as, for example, microdiscectomy instruments used to remove portions bulging or herniated discs and/or bone spurs, in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. In some embodiments, as used in the specification and including the appended claims, the term "tissue" includes soft tissue, ligaments, tendons, cartilage and/or bone unless specifically referred to otherwise.

The following discussion includes a description of a surgical system including a spinal construct, related components and methods of employing the surgical system in accordance with the principles of the present disclosure. Alternate embodiments are also disclosed. Reference is made in detail to the exemplary embodiments of the present disclosure, which are illustrated in the accompanying figures. Turning to FIGS. 1-5, there are illustrated components of a surgical system, such as, for example, a spinal implant system 10.

The components of spinal implant system 10 can be fabricated from biologically acceptable materials suitable for medical applications, including metals, synthetic polymers, ceramics and bone material and/or their composites. For example, the components of spinal implant system 10, individually or collectively, can be fabricated from materials such as stainless steel alloys, aluminum, commercially pure titanium, titanium alloys, Grade 5 titanium, super-elastic titanium alloys, cobalt-chrome alloys, superelastic metallic alloys (e.g., Nitinol, super elasto-plastic metals, such as GUM METAL®), ceramics and composites thereof such as calcium phosphate (e.g., SKELITE™), thermoplastics such as polyaryletherketone (PAEK) including polyetheretherketone (PEEK), polyetherketoneketone (PEKK) and polyetherketone (PEK), carbon-PEEK composites, PEEK-BaSO$_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyimide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tri-calcium phosphate (TCP), hydroxyapatite (HA)-TCP, calcium sulfate, or other resorbable polymers such as polyaetide, polyglycolide, polytyrosine carbonate, polycaroplaetohe and their combinations.

Various components of spinal implant system 10 may have material composites, including the above materials, to achieve various desired characteristics such as strength, rigidity, elasticity, compliance, biomechanical performance, durability and radiolucency or imaging preference. The components of spinal implant system 10, individually or collectively, may also be fabricated from a heterogeneous material such as a combination of two or more of the above-described materials. The components of spinal implant system 10 may be monolithically formed, integrally connected or include fastening elements and/or instruments, as described herein.

Figure 5:
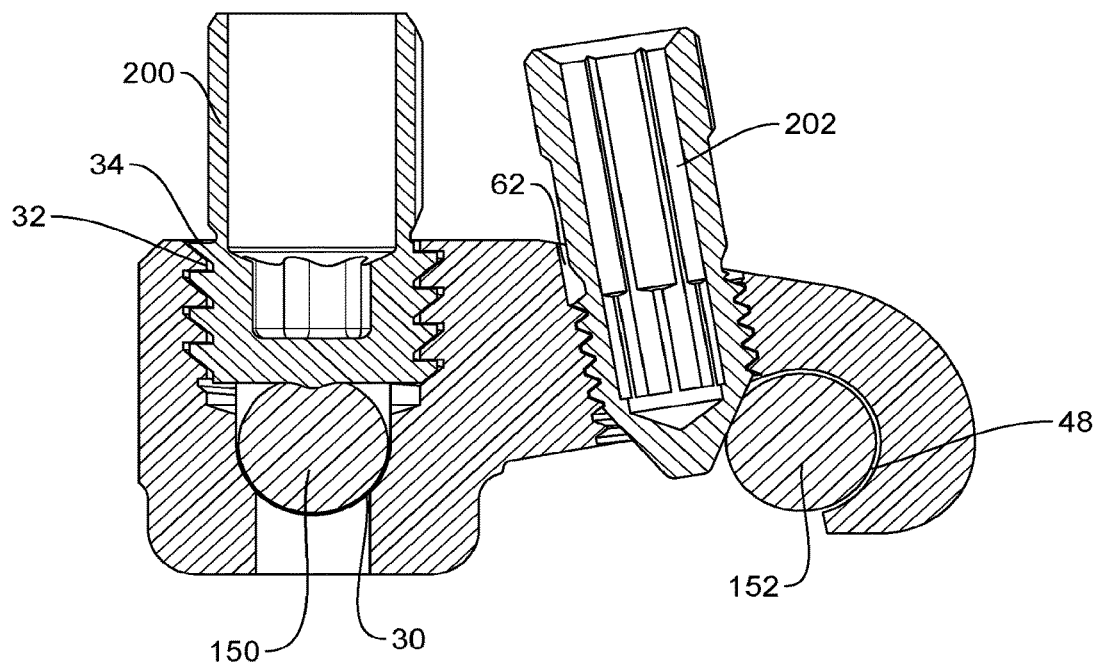
FIG. 5 is a side cross section view of the components shown in FIG. 1.
Figure 6:
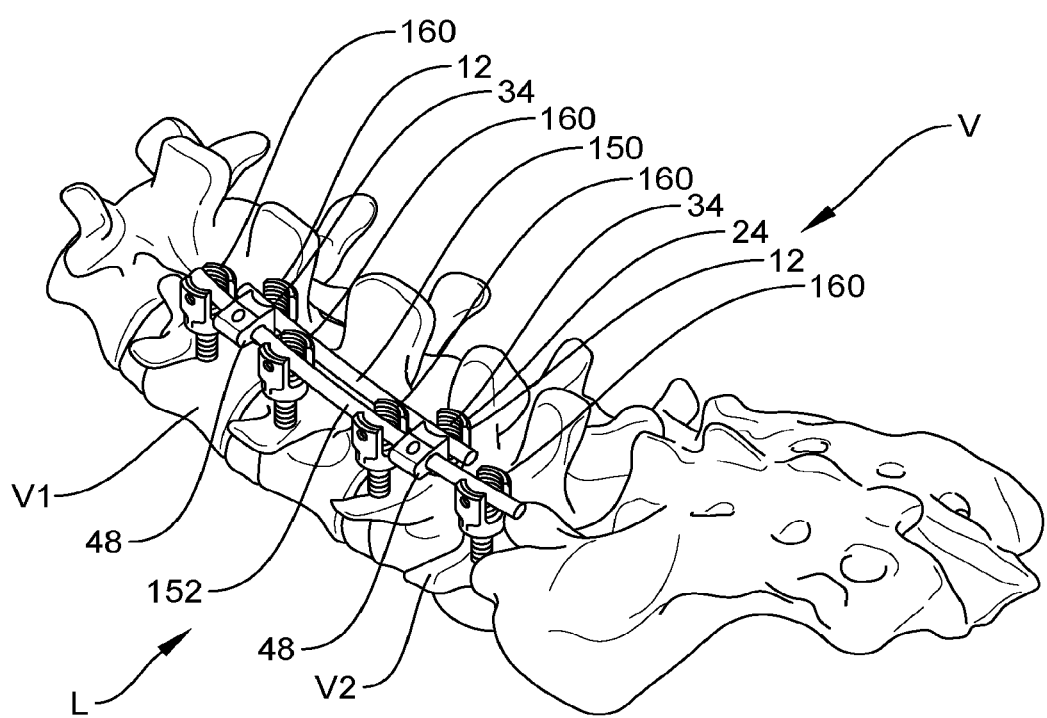
FIG. 6 is a perspective view of components of one embodiment of a system, disposed with vertebrae, in accordance with the principles of the present disclosure.

Spinal implant system 10 comprises a spinal construct including a connector 12. In some embodiments, connector 12 is configured to connect a first spinal rod 152 with bone screws 160 and a second spinal rod 150, as shown in FIGS. 1, 5, and 6.

Figure 2:
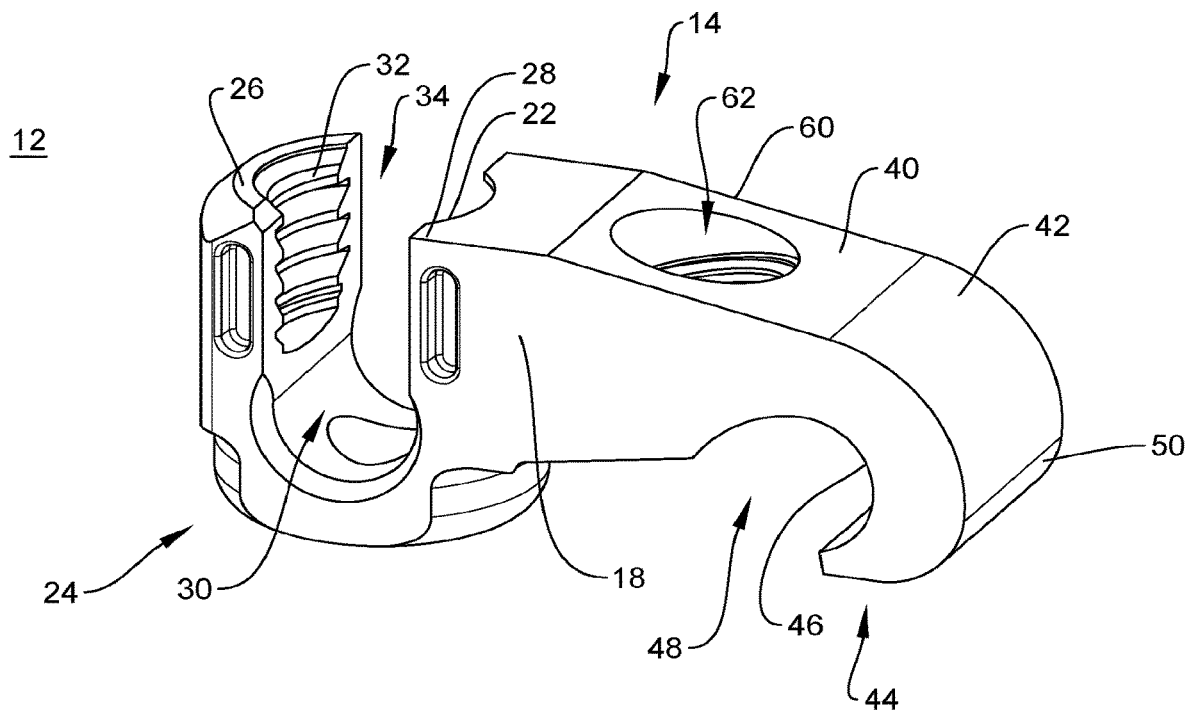
FIG. 2 is a perspective view of components of the system of FIG. 1.
Figure 3:
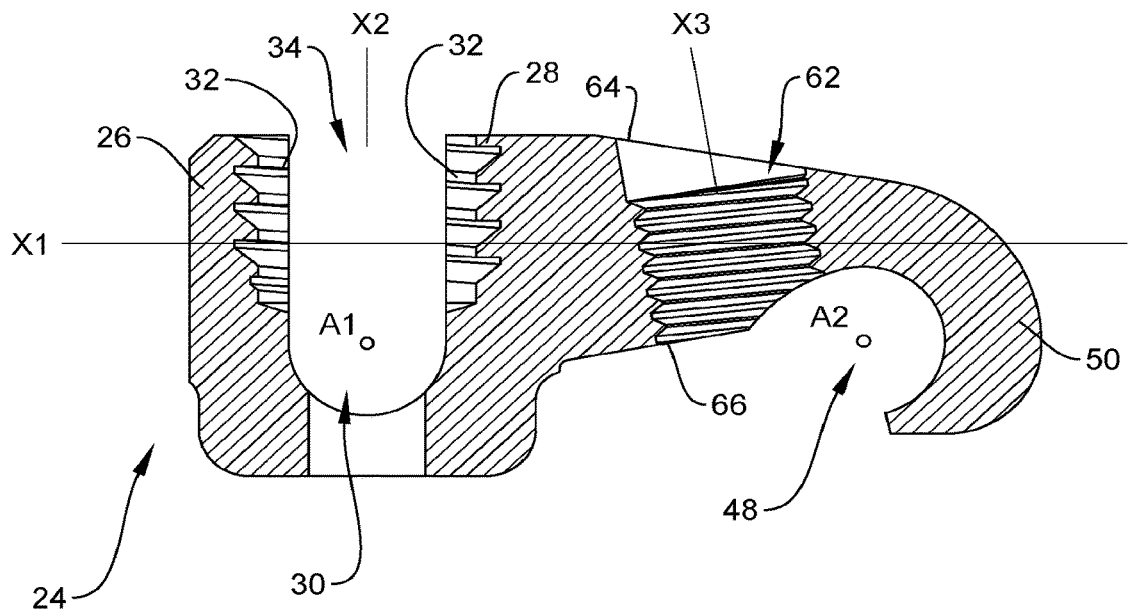
FIG. 3 is a side cross section view of the components shown in FIG. 2.
Figure 4:
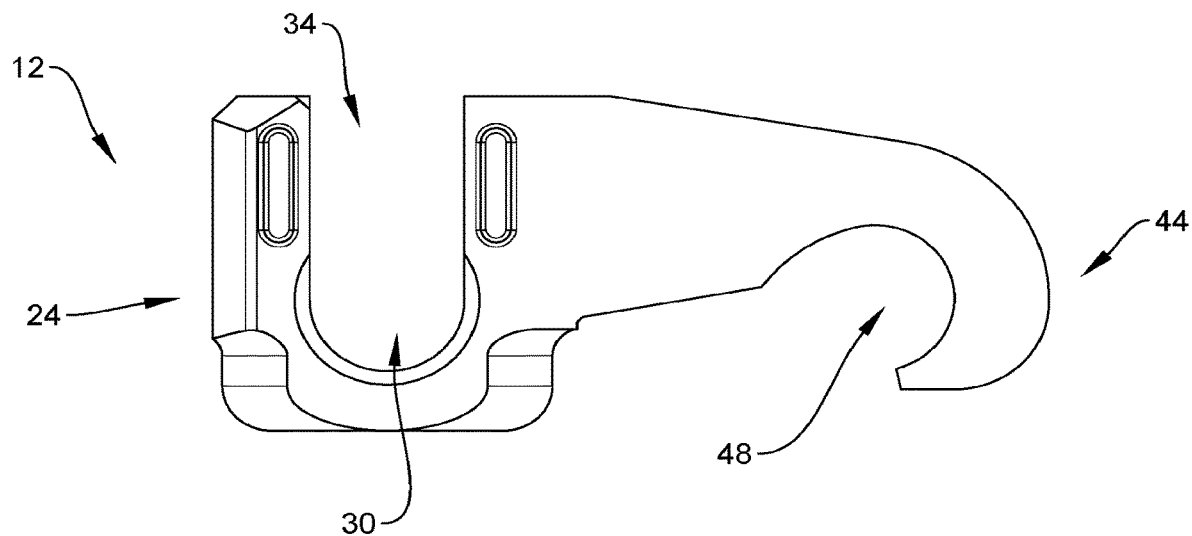
FIG. 4 is a side view of the components shown in FIG. 2.

Connector 12 includes a body 14 defining a transverse axis X1, as shown in FIG. 3. Body 14 includes a wall 18 (FIG. 2). Wall 18 includes a surface 22 that defines a portion of a cavity, such as for example, a receiver 24, as shown in FIG. 2. Receiver 24 includes a pair of spaced-apart arms 26, 28 that define an implant cavity, such as, for example, a passageway 30 therebetween. Passageway 30 is configured for top loading of a spinal implant, such as, for example, spinal rod 150, as shown in FIG. 1.

Arms 26, 28 each extend perpendicular to axis X1, as shown in FIG. 1. In some embodiments, arm 26 and/or arm 28 may be disposed at alternative orientations relative to axis X1, such as, for example, transverse and/or other angular orientations such as acute or obtuse, coaxial and/or may be offset or staggered. Arms 26, 28 each include an arcuate outer surface extending between a pair of side surfaces. In some embodiments, at least one of the outer surfaces and the side surfaces of arms 26, 28 have at least one recess or cavity therein configured to receive an insertion tool, compression instrument and/or instruments for manipulating connector 12.

Passageway 30 is substantially U-shaped. In some embodiments, all or only a portion of passageway 30 may have alternate cross-section configurations, such as, for example, closed, V-shaped, W-shaped, oval, oblong triangular, square, polygonal, irregular, uniform, non-uniform, offset, staggered, and/or tapered. In some embodiments, surface 48 includes gripping elements or surfaces, such as, for example, one or more surfaces being rough, arcuate, undulating, mesh, porous, semi-porous, dimpled and/or textured, to facilitate engagement with spinal rod 150. Passageway 30 defines an axis A1 that extends transverse to axis X1. In some embodiments, axis A1 may be disposed at alternate orientations, relative to axis X1, such as, for example, parallel, perpendicular and/or angular orientations such as acute or obtuse, coaxial and/or may be offset or staggered.

Receiver 24 includes threaded surfaces 32 that define an opening 34. Opening 34 extends along an axis X2, as shown in FIG. 3. Axis X2 is disposed in a substantially perpendicular orientation relative to axis X1. In some embodiments, axis X2 is disposed at alternate orientations, relative to axis X1, such as, for example, transverse and/or other angular orientations such as acute or obtuse, coaxial and/or may be offset or staggered. Opening 34 is disposed in communication with passageway 30 to facilitate fixation of spinal rod 150 with connector 12.

Surfaces 32 are configured for engagement with a coupling member, such as, for example, a set screw 200, to retain spinal rod 150 within passageway 30. In some embodiments, surfaces 32 is disposed with set screw 200 in alternate fixation configurations, such as, for example, friction fit, pressure fit, locking protrusion/recess, locking keyway and/or adhesive. In some embodiments, all or only a portion of surfaces 32 may have alternate surface configurations to enhance engagement with a spinal rod and/or a set screw such as, for example, rough, arcuate, undulating, mesh, porous, semi-porous, dimpled and/or textured.

Set screw 200 is configured for engagement with spinal rod 150 to facilitate fixation and/or locking of spinal rod 150 with receiver 24. Set screw 200 is disposable with receiver 24 between a non-locking orientation, such that spinal rod 150 is translatable relative to connector 12 and a locked orientation, such that set screw 200 fixes spinal rod 150 with connector 12.

Body 14 includes an extension 40. Extension 40 includes an end 42 forming a receiver 44. Receiver 44 includes a surface 46 that defines an implant cavity, such as, for example, a passageway 48. Receiver 44 includes an arcuate configuration, such as, for example, a hooked shaped wall 50 that defines passageway 48 and is configured to capture spinal rod 152. Receiver 44 is configured to facilitate side loading of spinal rod 152 with connector 12.

Passageway 48 is configured for side loading of spinal rod 152, as described herein. In some embodiments, passageway 48 is disposed separate and apart from passageway 30. In some embodiments, passageway 48 is disposed in a side by side orientation relative to passageway 30. In some embodiments, passageway 48 is disposed in a parallel orientation relative to passageway 30. In some embodiments, passageway 48 is disposed transverse to passageway 30. In some embodiments, passageway 48 is disposed in various orientations, such as, for example, perpendicular, transverse and/or at angular orientations such as acute or obtuse relative to passageway 30. In some embodiments, passageway 48 may be disposed offset or staggered from passageway 30.

In some embodiments, passageway 48 may have various cross section configurations, such as, for example, oval, oblong, triangular, rectangular, square, polygonal, irregular, uniform, non-uniform, variable and/or tapered. In some embodiments, surface 48 may includes gripping elements or surfaces, such as, for example, rough, arcuate, undulating, mesh, porous, semi-porous, dimpled and/or textured to facilitate engagement with spinal rod 152. Passageway 48 includes an axis A2 that extends transverse to axis X1. In some embodiments, axis A2 is disposed at alternate orientations, relative to axis X1, such as, for example, parallel, perpendicular and/or angular orientations such as acute or obtuse, coaxial and/or may be offset or staggered.

Extension 40 includes a threaded surface 60 that defines an opening 62. Opening 62 extends between an end 64 and an end 66 and extends along an axis X3, as shown in FIG. 3. Axis X3 is disposed in a substantially non-perpendicular orientation relative to axis X1. In some embodiments, axis X3 may be disposed at alternate orientations, relative to axis X1, such as, for example, perpendicular, transverse and/or other angular orientations such as acute or obtuse, coaxial and/or may be offset or staggered. Opening 62 is disposed in communication with passageway 48 to facilitate fixation of spinal rod 152 with connector 12.

Axis X3 is disposed in a non-parallel orientation relative to axis X2, as shown in FIG. 3. Opening 62 is oriented such that end 64 is angled towards opening 34 to facilitate insertion of connector 12. The configuration facilitates insertion of connector 12 into a patient through a smaller surgical incision made during a surgical procedure. In some embodiments, connector 12 may be utilized with a cortical screw trajectory procedure. In some embodiments, connector 12 facilitates connecting rods 150 each having a diameter of 4.75 mm by utilizing an angled opening 62 for connection of set screw 202 at side loaded spinal rod 152. Convergent angled set screws 200, 202 facilitate a midline type cortical bone screw trajectory, which maintains an orientation of the instruments throughout the procedure while minimizing tissue exposure.

Surface 60 is configured for engagement with a coupling member, such as, for example, a set screw 202, to retain spinal rod 152 within passageway 48. In some embodiments, surface 60 may be disposed with set screw 202 in alternate fixation configurations, such as, for example, friction fit, pressure fit, locking protrusion/recess, locking keyway and/or adhesive. In some embodiments, all or only a portion of surface 60 may have alternate surface configurations to enhance engagement with a spinal rod and/or a set screw such as, for example, rough, arcuate, undulating, mesh, porous, semi-porous, dimpled and/or textured.

Set screw 202 is configured for engagement with spinal rod 152 to facilitate fixation and/or locking of spinal rod 152 with receiver 44. Set screw 202 is disposable with receiver 44 between a non-locking orientation, such that spinal rod 152 is translatable relative to connector 12 and a locked orientation, such that set screw 202 fixes spinal rod 152 with connector 12.

In some embodiments, spinal implant system 10 can include one or a plurality of connectors 12 such as those described herein and/or fixation elements, which may be employed with a single vertebral level or a plurality of vertebral levels. In some embodiments, connectors 12 is engaged with vertebrae in various orientations, such as, for example, series, parallel, offset, staggered and/or alternate vertebral levels. In some embodiments, connectors 12 is configured as multi-axial screws, sagittal angulation screws, pedicle screws, mono-axial screws, uni-planar screws, fixed screws, anchors, tissue penetrating screws, conventional screws, expanding screws. In some embodiments, connectors 12 is employed with wedges, anchors, buttons, clips, snaps, friction fittings, compressive fittings, expanding rivets, staples, nails, adhesives, posts, connectors, fixation plates and/or posts.

In assembly, operation and use, spinal implant system 10, similar to the systems and methods described herein, is employed with a surgical procedure, such as, for example, a correction treatment of an applicable condition or injury of an affected section of a spinal column and adjacent areas within a body. Spinal implant system 10 may be completely or partially revised, removed or replaced.

In use, to treat a selected section of vertebrae V, including vertebrae V1, V2, as shown in FIG. 6, a medical practitioner obtains access to a surgical site including vertebrae V in any appropriate manner, such as through incision and retraction of tissues. In some embodiments, spinal implant system 10 can be used in any existing surgical method or technique including open surgery, mini-open surgery, minimally invasive surgery and percutaneous surgical implantation, whereby vertebrae V is accessed through a mini-incision, or a sleeve that provides a protected passageway to the area. Once access to the surgical site is obtained, the particular surgical procedure can be performed for treating the spine disorder.

An incision is made in the body of a patient and a cutting instrument (not shown) creates a surgical pathway for implantation of components of spinal implant system 10. A preparation instrument (not shown) can be employed to prepare tissue surfaces of vertebrae V, as well as for aspiration and irrigation of a surgical region.

Bone screws 160 are engaged with vertebrae V along a lateral side L of vertebrae V, as shown in FIG. 6. Bone screws 160 are manipulated to drive, torque, insert or otherwise connect bone screws 160 with vertebrae V. Spinal rod 150 is delivered along the surgical pathway to a surgical site adjacent vertebrae V. Spinal rod 150 is disposed with bone screws 160 along vertebrae V. Connectors 12 are disposed adjacent spinal rod 150. Each connector 12 is manipulated to dispose spinal rod 150 with passageway 30 from a top loading orientation.

Spinal rod 150 is fixed with receiver 24 by engaging set screw 200 with surface 32 of opening 34. Set screw 34 is engaged with a surgical instrument, such as, for example, a driver (not shown), which advances set screw 200 along axis X2 into engagement with surface 32 in a locking orientation, as described herein. The driver engages set screw 200 to fix spinal rod 150 with receiver 24 and for attachment of spinal rod 150 with vertebrae V.

Spinal rod 152 is delivered along the surgical pathway to a surgical site adjacent vertebrae V. Spinal rod 152 is disposed with passageway 48 from a side loading orientation. Set screw 202 is disposed with opening 62 and engaged with surface 60 along axis X3. Set screw 202 is engaged with a surgical instrument, such as, for example, a driver (not shown), which advances set screw 202 into opening 62 in a non-locking orientation, as described herein. Spinal rod 152 is translatable relative to connector 12 to position spinal rod 152 relative to spinal rod 150 and connector 12. The driver engages set screw 202 to fix spinal rod 152 with connector 12 and for attachment of spinal rod 152 with vertebrae V. In some embodiments, spinal rod 152 is configured to share the load applied to spinal rod 150. In some embodiments, spinal rod 152 is configured to extend spinal rod 150 to an adjacent vertebral level. Spinal rod 152 is configured to add support and strength to spinal implant system 10 along vertebrae V.

In some embodiments, spinal implant system 10 includes a second set of connectors 12, bone screws 160 and spinal rods 150, 152 (not shown) delivered along the surgical pathway to the surgical site adjacent a contra-lateral side of vertebrae V. The second set of connectors 12, bone screws 160 and spinal rods 150, 152 are connected with the contra-lateral side of vertebrae V, similar to lateral side L described herein. In some embodiments, the spinal constructs of spinal implant system 10, as described herein, are fixed with vertebrae V in a side by side orientation and/or a bi-lateral arrangement to stabilize vertebrae V and affect growth for a correction treatment to treat spine pathologies, as described herein. In some embodiments, one or all of the components of spinal implant system 10 can be delivered or implanted as a pre-assembled device or can be assembled in situ, in a selected order of assembly or the order of assembly of the particular components of spinal implant system 10 can be varied according to practitioner preference, patient anatomy or surgical procedure parameters.

Upon completion of the procedure, the surgical instruments, assemblies and non-implanted components of spinal implant system 10 are removed from the surgical site and the incision is closed. One or more of the components of spinal implant system 10 can be made of radiolucent materials such as polymers. Radiomarkers may be included for identification under x-ray, fluoroscopy, CT or other imaging techniques. In some embodiments, the use of surgical navigation, microsurgical and image guided technologies is employed to access, view and repair spinal deterioration or damage, with the aid of spinal implant system 10.

In some embodiments, spinal implant system 10 includes an agent, which may be disposed, packed, coated or layered within, on or about the components and/or surfaces of spinal implant system 10. In some embodiments, the agent may include bone growth promoting material, such as, for example, bone graft to enhance fixation of the bone fasteners with vertebrae. In some embodiments, the agent may include one or a plurality of therapeutic agents and/or pharmacological agents for release, including sustained release, to treat, for example, pain, inflammation and degeneration.

Figure 7:
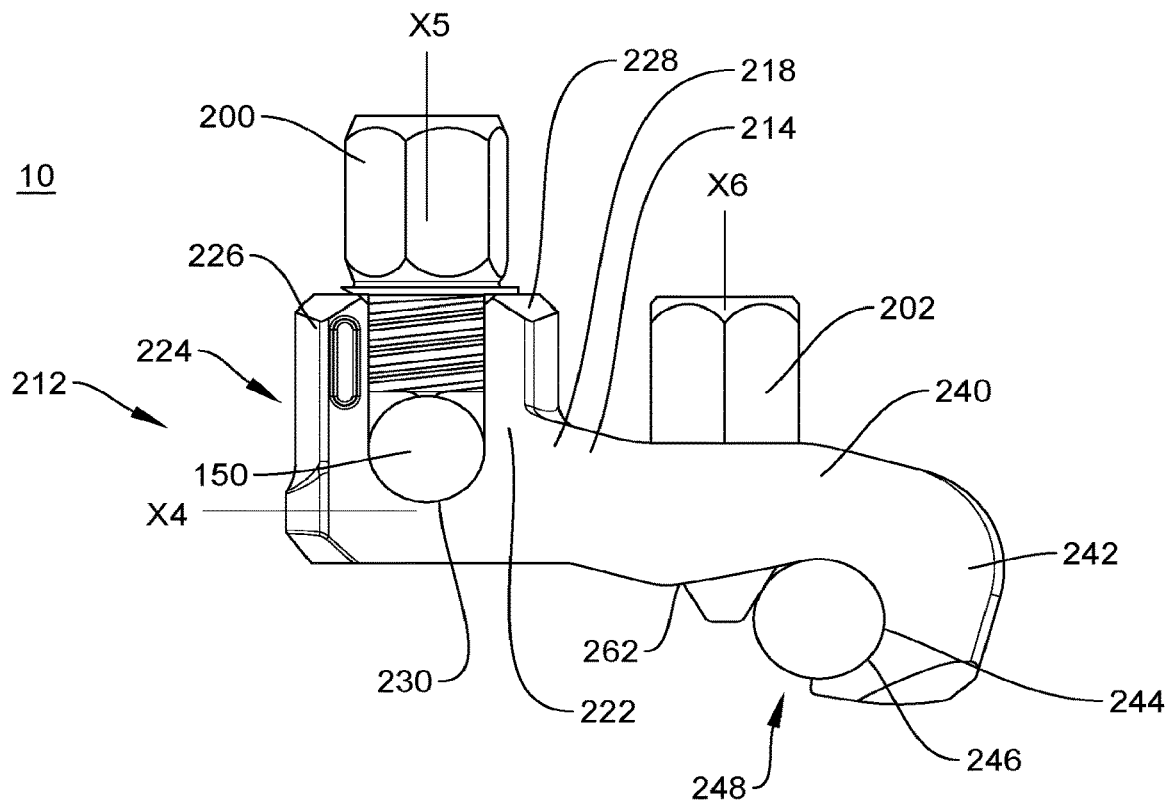
FIG. 7 is a side view of components of another embodiment of a system in accordance with the principles of the present disclosure.
Figure 8:
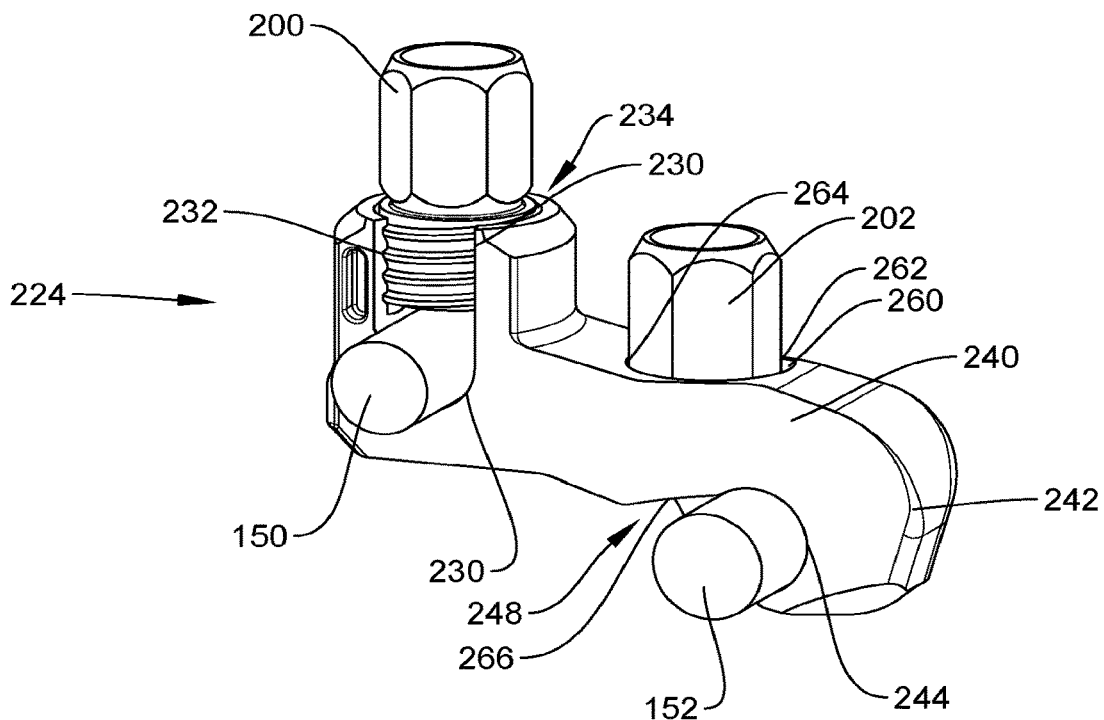
FIG. 8 is a perspective view of the components shown in FIG. 7.
Figure 9:
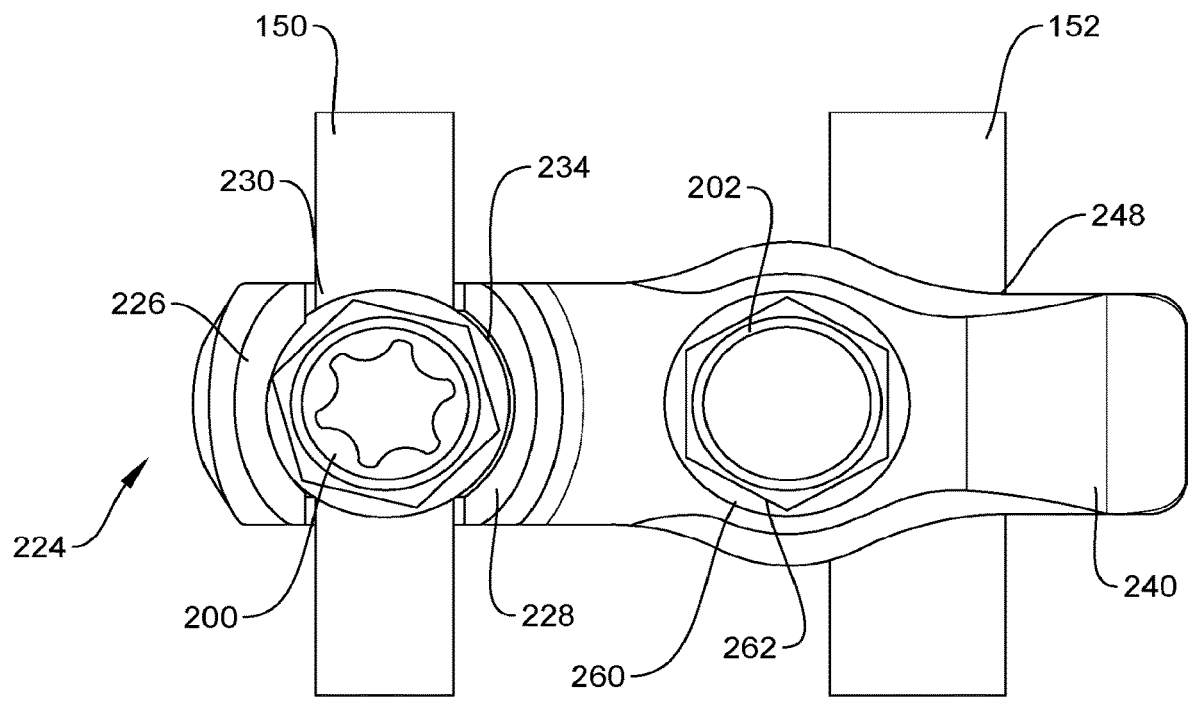
FIG. 9 is a top view of the components shown in FIG. 7.

In one embodiment, as shown in FIGS. 7-9, spinal implant system 10, similar to the systems and methods described herein, includes a connector 212, similar to connector 12 described herein.

Connector 212 includes a body 214 defining a transverse axis X4, as shown in FIG. 7. Body 214 includes a wall 218. Wall 218 includes a surface 222 that defines a portion of a cavity, such as for example, a receiver 224, similar to receiver 24 as described herein. Receiver 224 includes a pair of spaced apart arms 226, 228 that define an implant cavity, such as, for example, a passageway 230 therebetween. Passageway 230 is configured for top loading of spinal rod 150, as described herein. Arms 226, 228 each extend along an axis X5 in a non-perpendicular orientation relative to axis X4, as shown in FIG. 7.

Receiver 224 includes threaded surfaces 232 that define an opening 234. Opening 234 extends along axis X5 such that opening 234 extends X5 in a non-perpendicular orientation relative to axis X4. In some embodiments, axis X5 may be disposed at alternate orientations, relative to axis X4, such as, for example, perpendicular, transverse and/or other angular orientations such as acute or obtuse, coaxial and/or may be offset or staggered. Opening 234 is disposed in communication with passageway 230 to facilitate fixation of spinal rod 150 with connector 212. Surfaces 232 are configured for engagement with set screw 200, as described herein, to retain spinal rod 150 within passageway 230.

Body 214 includes an extension 240. Extension 240 includes an end 242 forming a receiver 244. Receiver 244 includes a surface 246 that defines a passageway 248. Receiver 244 includes a hooked shaped wall 250 that defines passageway 248 and configured to capture spinal rod 152. Receiver 244 is configured to facilitate side loading of spinal rod 152.

Passageway 248 is configured for side loading of spinal rod 152, as described herein. In some embodiments, passageway 248 is disposed separate and apart from passageway 230. In some embodiments, passageway 248 is disposed in a side by side orientation relative to passageway 230. In some embodiments, passageway 248 is disposed in a parallel orientation relative to passageway 230. In some embodiments, passageway 248 is disposed transverse to passageway 230. In some embodiments, passageway 248 is disposed in various orientations, such as, for example, perpendicular, transverse and/or at angular orientations, such as acute or obtuse relative to passageway 230. In some embodiments, passageway 248 is disposed offset or staggered from passageway 230. In some embodiments, passageway 248 may have various cross section configurations, such as, for example, oval, oblong, triangular, rectangular, square, polygonal, irregular, uniform, non-uniform, variable and/or tapered. In some embodiments, surface 248 may include gripping elements or surfaces, such as, for example, rough, arcuate, undulating, mesh, porous, semi-porous, dimpled and/or textured to facilitate engagement with spinal rod 152.

Extension 240 includes a threaded surface 260 that defines an opening 262. Opening 262 extends between an end 264 and an end 266 and extends along an axis X6, as shown in FIG. 7. Axis X6 is disposed in a substantially non-perpendicular orientation relative to axis X4. In some embodiments, axis X6 is disposed at alternate orientations, relative to axis X4, such as, for example, perpendicular, transverse and/or other angular orientations such as acute or obtuse, coaxial and/or may be offset or staggered. Opening 262 is disposed in communication with passageway 248 to facilitate fixation of spinal rod 152 with connector 212. Axis X6 is disposed in a parallel orientation relative to axis X4 such that opening 234 is disposed parallel relative to opening 262. Opening 262 is oriented such that end 264 is angled towards opening 234 to facilitate insertion of connector 212 through a smaller incision in a patient, as described herein.

Surface 260 is configured for engagement with a set screw 202, as described herein, to retain spinal rod 152 within passageway 248. Set screw 202 is configured for engagement with spinal rod 152 to facilitate fixation and/or locking of spinal rod 152 with receiver 244. Set screw 202 is disposable with receiver 244 between a non-locking orientation, such that spinal rod 152 is translatable relative to connector 212 and a locked orientation, such that set screw 202 fixes spinal rod 152 with connector 212.

In one embodiment, as shown in FIGS. 10-14, spinal implant system 10, similar to the systems and methods described herein, includes a connector 312, similar to connector 12 described herein.

Figure 10:
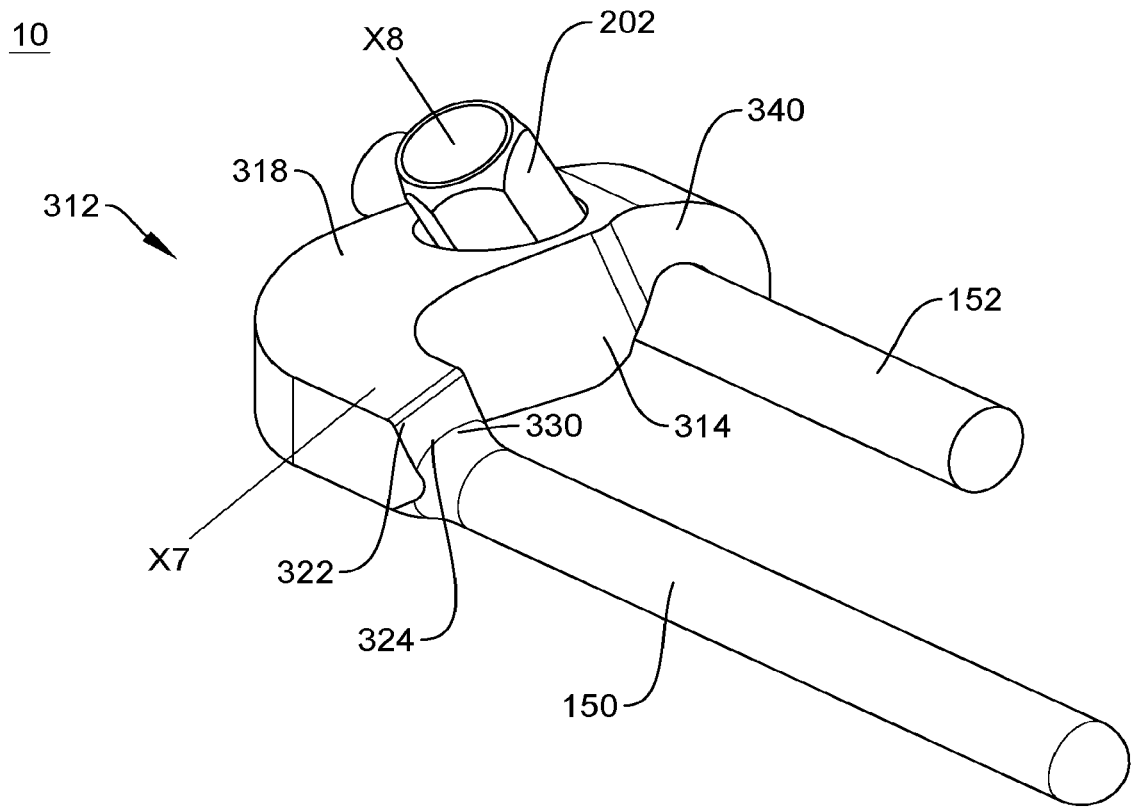
FIG. 10 is a perspective view of components of a third embodiment of a system in accordance with the principles of the present disclosure.
Figure 11:
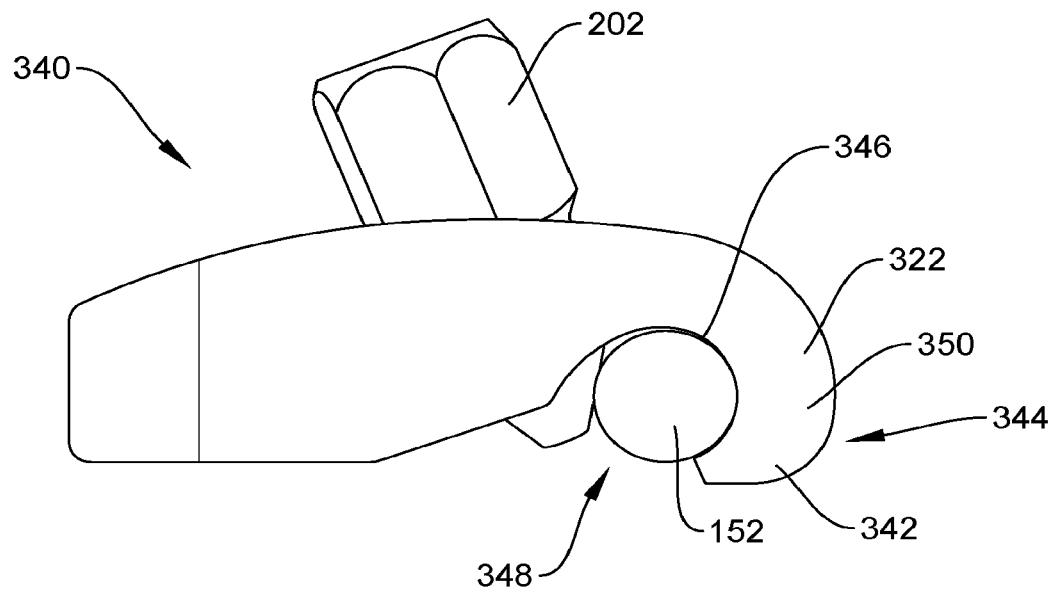
FIG. 11 is a break-away view of the components shown in FIG. 10.

Connector 312 includes a body 314 defining a transverse axis X7, as shown in FIG. 10. Body 314 includes a wall 318. Wall 318 includes a surface 322 that defines a portion of a cavity, such as for example, a closed receiver 324. In some embodiments, receiver 324 includes a passageway 330 for disposal of an end of spinal rod 150. In some embodiments, spinal rod 150 is monolithically formed with receiver 324. In some embodiments, spinal rod 150 is integrally connected with receiver 324. In some embodiments, spinal rod 324 is attached with receiver 324 with fastening elements and/or instruments.

Body 314 includes an extension 340. Extension 340 includes an end 342 forming a receiver 344. Receiver 344 includes a surface 346 that defines a passageway 348. Receiver 344 includes a hooked shaped wall 350 that defines passageway 348 and configured to capture spinal rod 152. Receiver 344 is configured to facilitate side loading of spinal rod 152.

Passageway 348 is configured for side loading of spinal rod 152, as described herein. In some embodiments, passageway 348 positions spinal rod 152 separate and apart from spinal rod 150. In some embodiments, passageway positions spinal rod 152 in a side by side orientation relative to spinal rod 150. In some embodiments, passageway 348 positions spinal rod 152 in a parallel orientation relative to spinal rod 150. In some embodiments, passageway 348 positions spinal rod 152 transverse to spinal rod 150. In some embodiments, passageway 348 may position spinal rod 152 in various orientations, such as, for example, perpendicular, transverse and/or at angular orientations, such as acute or obtuse relative to spinal rod 150. In some embodiments, passageway 348 may position spinal rod 152 offset or staggered from spinal rod 150. In some embodiments, passageway 348 may have various cross section configurations, such as, for example, oval, oblong, triangular, rectangular, square, polygonal, irregular, uniform, non-uniform, variable and/or tapered. In some embodiments, surface 348 may include gripping elements or surfaces, such as, for example, rough, arcuate, undulating, mesh, porous, semi-porous, dimpled and/or textured to facilitate engagement with spinal rod 152.

Figure 12:
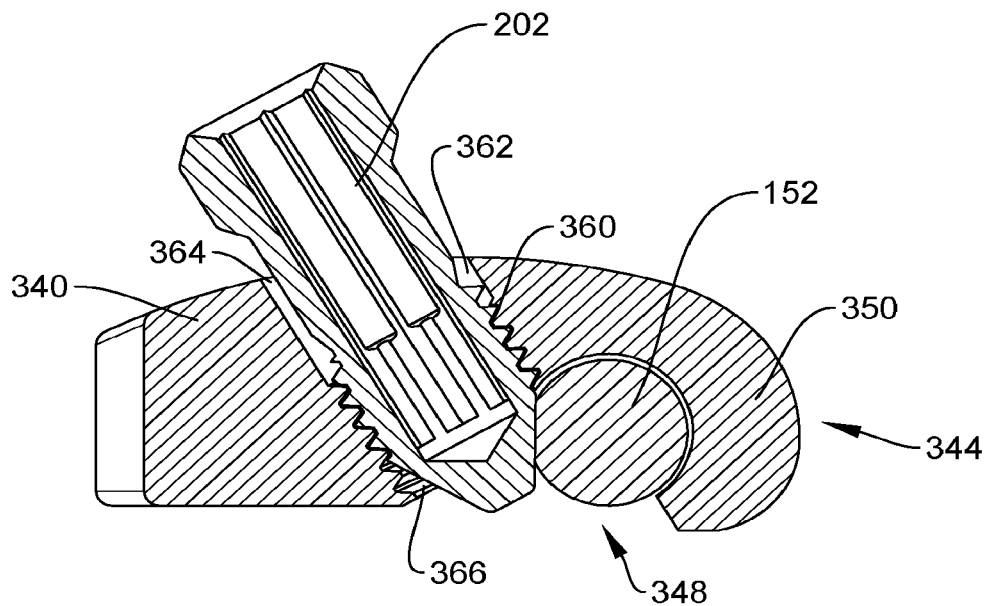
FIG. 12 is a cross section view of the components shown in FIG. 11.
Figure 13:
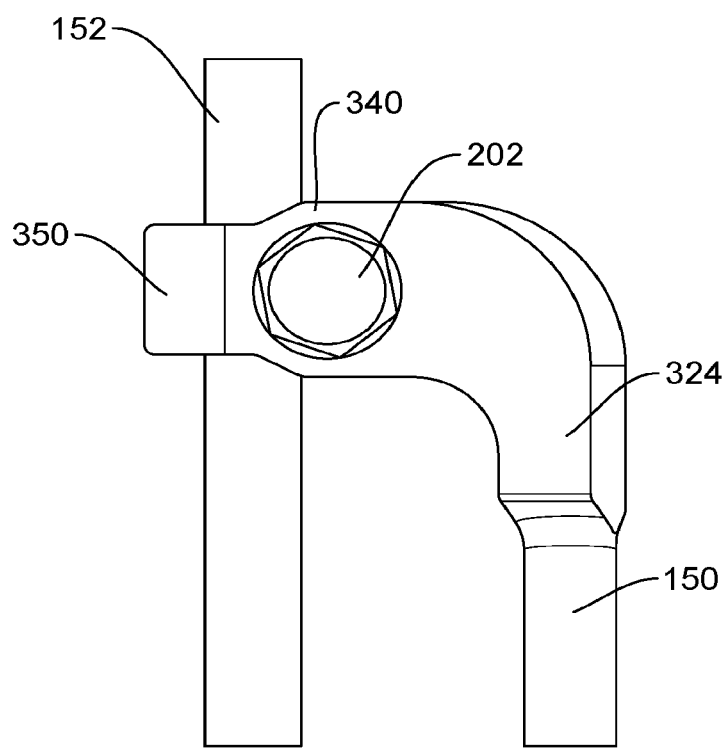
FIG. 13 is a top view of the components shown in FIG. 10.
Figure 14:
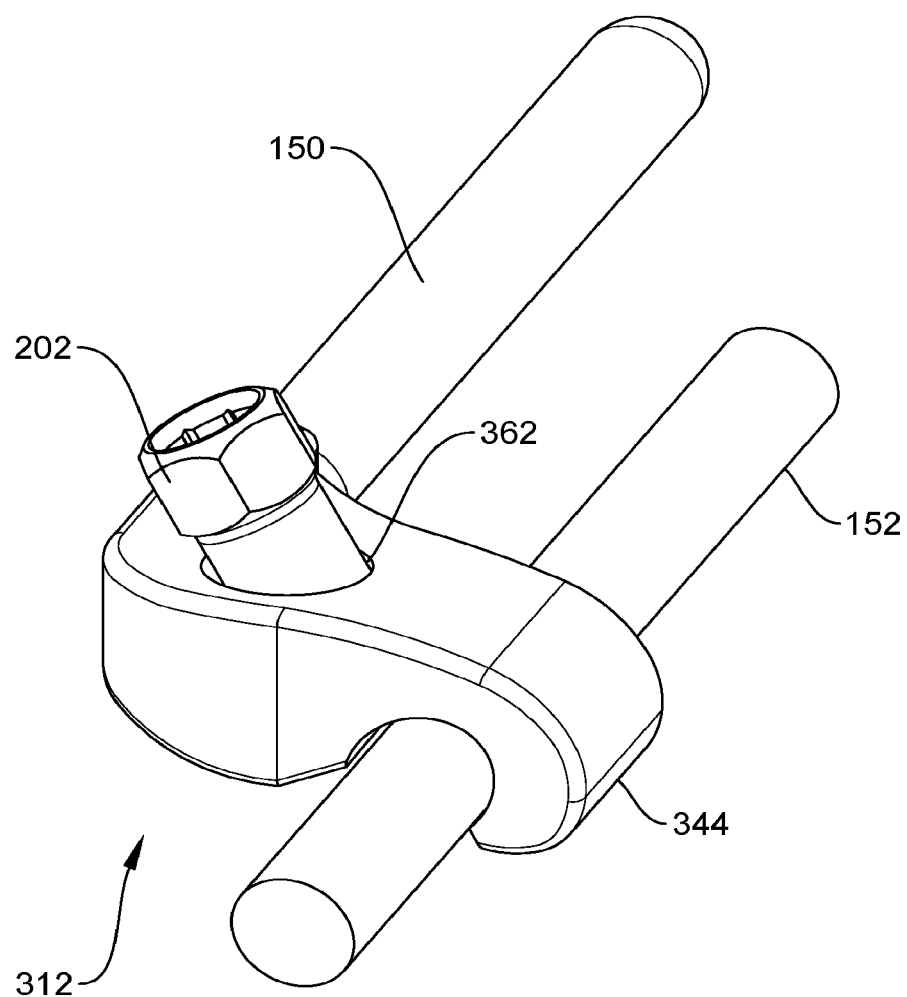
FIG. 14 is another perspective view of the components shown in FIG. 10.

Extension 340 includes a threaded surface 360 that defines an opening 362, as shown in FIG. 12. Opening 362 extends between an end 364 and an end 366 and extends along an axis X8, as shown in FIG. 12. Axis X8 is disposed in a substantially non-perpendicular orientation relative to axis X7. In some embodiments, axis X8 may be disposed at alternate orientations, relative to axis X7, such as, for example, perpendicular, transverse and/or other angular orientations such as acute or obtuse, coaxial and/or may be offset or staggered. Opening 362 is disposed in communication with passageway 348 to facilitate fixation of spinal rod 152 with connector 312. Opening 362 is oriented such that end 364 is angled towards receiver 324 to facilitate insertion of connector 312 through a smaller incision in a patient, as described herein.

Surface 360 is configured for engagement with a set screw 202, as described herein, to retain spinal rod 152 within passageway 348. Set screw 202 is configured for engagement with spinal rod 152 to facilitate fixation and/or locking of spinal rod 152 with receiver 344. Set screw 202 is disposable with receiver 344 between a non-locking orientation, such that spinal rod 152 is translatable relative to connector 212 and a locked orientation, such that set screw 202 fixes spinal rod 152 with connector 312.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A spinal construct comprising a body, the body extending between opposite first and second ends and including opposite proximal and distal surfaces, the construct comprising a first arm extending from the first end and a second arm extending from the second end, the proximal surface and inner surfaces of the arms defining a first implant cavity, the construct comprising an extension extending from the second arm, an end of the extension defining a second implant cavity, the construct including a first opening communicating with the first implant cavity and a second opening communicating with the second implant cavity, the first opening defining a first axis and the second opening defining a second axis, the second axis being disposed in a non-parallel orientation relative to the first axis such that the second opening is angled toward the first opening, a portion of the end of the extension that defines the second implant cavity extending perpendicular to the first axis.

2. The spinal construct recited in claim 1, wherein the first axis extends through the first implant cavity and the second axis is spaced apart from the second implant cavity.

3. The spinal construct recited in claim 1, wherein the construct comprises a bore extending through the proximal and distal surfaces of the body.

4. The spinal construct recited in claim 3, wherein the bore is coaxial with the first axis.

5. The spinal construct recited in claim 1, wherein the inner surfaces of the arms are threaded for engagement with threads of a setscrew.

6. The spinal construct recited in claim 1, wherein the second opening includes a proximal portion and a distal portion, the proximal portion being unthreaded, the distal portion comprising a female thread configured for engagement with threads of a setscrew.

7. The spinal construct recited in claim 1, further comprising:
a first setscrew threaded with threads defined by the inner surfaces of the arms; and
a second setscrew threaded with a threaded surface that defines a portion of the second opening.

8. The spinal construct recited in claim 7, wherein:
the first setscrew is coaxial with the first axis; and
the second setscrew is coaxial with the second axis.

9. The spinal construct recited in claim 1, further comprising a setscrew disposable with the first opening such that the setscrew is coaxial with the first axis and is engageable with a spinal rod disposed with the first implant cavity.

10. The spinal construct recited in claim 1, wherein the end of the extension comprises a hook that includes the portion and defines the second implant cavity.

11. The spinal construct recited in claim 10, wherein the body is disposed in a first transverse plane and a tip of the hook is disposed in a second transverse plane, the second transverse plane extending parallel to the first transverse plane and being disposed proximal to the first transverse plane, the transverse planes each extending perpendicular to the first axis.

12. The spinal construct recited in claim 1, wherein the first implant cavity is disposed in a first transverse plane and the second implant cavity is disposed in a second transverse plane, the second transverse plane extending parallel to the first transverse plane and being disposed proximal to the first transverse plane, the transverse planes each extending perpendicular to the first axis.

13. The spinal construct recited in claim 1, wherein the second opening extends through opposite proximal and distal surfaces of the extension, the proximal and distal surfaces of the extension each extending at an acute angle relative to the first axis.

14. The spinal construct recited in claim 1, wherein a proximal end of the second arm is continuous with a proximal surface of the extension.

15. The spinal construct recited in claim 1, wherein the second implant cavity is in communication with a third opening that faces the body, the third opening being spaced apart from the second opening.

16. The spinal construct recited in claim 1, wherein the first opening defines a proximal opening of the first implant cavity and a third opening of the construct defines a distal opening of the second implant cavity, the third opening being spaced apart from the second opening.

17. The spinal construct recited in claim 1, wherein the construct is configured to have a first rod moved distally into the first implant cavity and to have a second rod moved proximally into the second implant cavity.

18. The spinal construct recited in claim 1, wherein the distal surface is planar and extends perpendicular to the first axis.

19. A spinal construct comprising a body, the body extending between opposite first and second ends and comprising opposite proximal and distal surfaces, the construct comprising a first arm extending from the first end and a second arm extending from the second end, the proximal surface and inner surfaces of the arms defining a first implant cavity, the construct comprising an extension extending from the second arm, an end of the extension defining a second implant cavity, the construct including a first opening communicating with the first implant cavity and a second opening communicating with the second implant cavity, the first opening defining a first axis and the second opening defining a second axis, the second axis being disposed in a non-parallel orientation relative to the first axis such that the second opening is angled toward the first opening, a portion of the end of the extension that defines the second implant cavity extending perpendicular to the first axis, wherein the construct comprises a circular bore extending through the proximal and distal surfaces of the body, the bore being coaxial with the first axis, wherein the inner surfaces of the arms are threaded for engagement with threads of a setscrew, and wherein the second opening includes a proximal portion and a distal portion, the proximal portion being unthreaded, the distal portion comprising a female thread.

20. A spinal construct comprising:

a body extending between opposite first and second ends and comprising opposite proximal and distal surfaces, the construct comprising a first arm extending from the first end and a second arm extending from the second end, the proximal surface and inner surfaces of the arms defining a first implant cavity, the inner surfaces of the arms being threaded for engagement with threads of a setscrew, the construct comprising an extension extending from the second arm, an end of the extension defining a second implant cavity, the construct including a first opening communicating with the first implant cavity and a second opening communicating with the second implant cavity, the second opening including a proximal portion and a distal portion, the proximal portion being unthreaded, the distal portion comprising a female thread, the first opening defining a first axis and the second opening defining a second axis, the second axis being disposed in a non-parallel orientation relative to the first axis such that the second opening is angled toward the first opening and the second axis is inclined toward the first axis, a portion of the end of the extension that defines the second implant cavity extending perpendicular to the first axis;

a first setscrew threaded with the threads defined by the inner surfaces of the arms such that the first setscrew is coaxial with the first axis; and a second setscrew threaded with the female thread such that the second setscrew is coaxial with the second axis.

* * * * *